(12) United States Patent
Hamada et al.

(10) Patent No.: US 7,303,541 B2
(45) Date of Patent: Dec. 4, 2007

(54) METHOD FOR TESTING PERITONEAL FUNCTION

(75) Inventors: Hiroyuki Hamada, Fukuoka (JP); Shinji Namoto, Hatsukaichi (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 10/520,330

(22) PCT Filed: Jul. 8, 2003

(86) PCT No.: PCT/JP03/08638

§ 371 (c)(1), (2), (4) Date: Jan. 5, 2005

(87) PCT Pub. No.: WO2004/006776

PCT Pub. Date: Jan. 22, 2004

(65) Prior Publication Data

US 2005/0244909 A1    Nov. 3, 2005

(30) Foreign Application Priority Data

Jul. 10, 2002    (JP) .............................. 2002-201820

(51) Int. Cl.
*A61M 1/00* (2006.01)
(52) U.S. Cl. ............................. 604/29; 604/28; 604/27
(58) Field of Classification Search ..................... None
See application file for complete search history.

(56) References Cited

U.S. PATENT DOCUMENTS 5,670,057 A * 9/1997 Chen et al. .................. 210/739

6,077,836 A * 6/2000 Milner ......................... 514/54

OTHER PUBLICATIONS

Kelton et al. Comparison of Chemical Composition of Peritoneal Fluid and Serum: A Method for Monitoring Dialysis Patients and a Tool for Asesing Binding to Serum Proteins in Vivo; Ann. Intern. Med., vol. 89, Issue 1 (1978) pp. 67-70.*

* cited by examiner

*Primary Examiner*—Jon Weber
*Assistant Examiner*—Paul Martin
(74) *Attorney, Agent, or Firm*—Hamre, Schumann, Mueller & Larson, P.C.

(57) ABSTRACT

The peritoneal function of a peritoneal dialysis patient is examined to evaluate the condition of the patient. An examining method comprises a step of alternately repeating introduction/drainage of a predetermined quantity of a peritoneal dialyzing fluid of an osmotic pressure and introduction/drainage of a predetermined quantity of another peritoneal dialyzing fluid of an osmotic pressure different from the former one, a step of examining the drain to determine the quantity of peritoneal dialyzing fluid staying in the abdominal cavity of the patient and the concentration of a solute of interest, a step of conducting a peritoneal equilibrium test, and a step of conducting a blood test to grasp the change of the state of the blood caused by the introduction and drainage. The blood test step is executed only once. The current states of the peritoneal dialysis capability and the water removal capability of the patient can be efficiently and accurately evaluated so as to carry out peritoneal dialysis most suitable for the condition of the patient.

3 Claims, 3 Drawing Sheets

METHOD FOR TESTING PERITONEAL FUNCTION

TECHNICAL FIELD

The present invention relates to a method for testing peritoneal dialysis function and water removal function, so as to evaluate efficiently and accurately the current state of the peritoneal function in patients with chronic renal failure, in order to perform a peritoneal dialysis that is optimal for the condition of that patient.

BACKGROUND ART

One of the most important issues in conventional medical treatment of peritoneal dialysis has been how to correctly determine the peritoneal dialysis state and the peritoneal permeability of peritoneal dialysis patients so as to evaluate the peritoneal function and determine the optimum dialysis conditions. For example, with Continuous Ambulatory Peritoneal Dialysis (CAPD), which is a so-called chronic peritoneal dialysis treatment that was proposed in the 1970s, approximately two liters of peritoneal dialysis fluid is retained within the abdominal cavity for five to six hours, and is exchanged from four to six times daily. Also, to maintain constancy within the patient's body, the dialysis function and water removal function (hereinafter, collectively referred to as "peritoneal function") of the patient's peritoneum is evaluated, and the most suitable dialysis fluid exchange schedule (hereinafter, referred to as "dose") based on that evaluation is set.

However, during the 1970s, which is when CAPD was proposed, very little was known of the characteristics of peritoneal function and the change over time in peritoneal function over the course of peritoneal dialysis, and thus there was no established testing method for appropriately evaluating peritoneal function, and the dose was set based on physician experience and judgment.

By the 1980s, as the number of clinical cases increased, it became clear that peritoneal function differed for each patient, and methods for testing peritoneal function involving qualitative evaluation of dialysis function and water removal function were proposed. Peritoneal Equilibrium Test (hereinafter, also referred to as "PET") is one of the most frequently used qualitative evaluation methods. With PET, peritoneal function is divided into four categories, these being good, moderately good, moderately poor, and poor, and a general dose pattern that is considered appropriate is proposed for each category.

By the 1990s, it was shown that there are limitations to the patients for which qualitative evaluation methods may be adopted, and quantitative evaluation methods that take patient body type into account were proposed. The quantitative evaluation method uses creatinine clearance, which is one index for the dialysis amount of chronic peritoneal dialysis patients, urea Kt/V, and statistical results on survival rates, as criteria. The dose that satisfies the quantitative criteria of these two parameters with respect to survival rate is judged to be the optimum dosage. By using the above qualitative evaluation method and this quantitative evaluation in tandem, it became possible to determine the optimum dose pattern and dose.

The use of these two evaluation methods in tandem, however, at most results in only an evaluation of the suitability of a dose at various points. Consequently, the setting of the dose was performed by trial and error, and there was the problem that the physician had only his experience to rely on when setting a dose.

Accordingly, a computer simulation that builds a mathematical model of chronic peritoneal dialysis methods and proposes the most suitable dose based on analysis of the speed at which the peritoneum moves substances was proposed. Using computer simulation made it possible to propose a dose suited for the peritoneal function of the patient by adopting both the dose pattern proposed by qualitative evaluation and the criteria indicated by quantitative evaluation.

However, there was no effective and economical clinical data collection protocol (testing method) for collecting the data necessary for this analysis. Although numerous clinical data collection protocols (testing methods) for implementing computer simulation have been proposed, each of the methods takes the body's circadian rhythm into consideration and measures the material balance of monitored solutes (such as urine toxins) and the uptake and release of water over a 24-hour period.

FIG. 1 shows an example of the procedure of a conventional method for testing peritoneal function. The horizontal axis shows the time elapsed from the start of testing. "Fluid infusion" and "fluid drain" in accordance with the passage of time are shown. Also, the timing of a body weight measurement 11, a blood draw 12, a urine storage 13, and a urine test 14 are shown in relation to "fluid infusion" and "fluid drain."

As shown in FIG. 1, to detect the material balance of monitored solutes (such as urine toxins) and the uptake and release of water over a 24-hour period, first, infusion of a low osmotic pressure fluid (360 (units are mOsm/kg-solvent; same below)), which is a dialysis fluid having a low osmotic pressure, is begun in the evening (22:30) two days prior to the day on which testing is finished. The next morning the fluid is drained and a first blood sample 12 (8:00) is taken.

Next, a body weight measurement 11 is performed, and then a medium osmotic fluid (400), which is a dialysis fluid having a high osmotic pressure, is infused, and for the peritoneal equilibrium test (PET), the fluid is drained, some is sampled, and then is returned two times at predetermined time intervals, after which the fluid is finally drained. It should be noted that in general PET is performed using a medium osmotic pressure fluid (400). Also, PET is a test that should be performed in the hospital, and the second blood sample 12 is generally taken while the patient is in the hospital. After that the dialysis fluid is infused and drained, and when the final fluid drain is complete (8:00), a third blood sample 12 is taken and a urine test 14 is performed.

In this testing procedure, the patient was forced to stay in the hospital because it was necessary to take a blood sample and perform a PET. In other words, in the above test, several blood samples are taken during a 24-hour period. It was therefore frequently necessary to admit patients to the hospital, depending on their living environment, and this was a problem because it imposed time constraints on patients and left them mentally fatigued.

There was also the problem that the large number of tests placed a large time and work burden on the patient and medical staff, and in spite of this, it was difficult to gather data that accurately reflected the normal daily condition of the patient.

DISCLOSURE OF THE INVENTION

The object of the present invention is to provide a method for testing peritoneal function with which it is possible to efficiently and accurately evaluate the current condition of the peritoneal dialysis function and the water removal function of a patient, such that peritoneal dialysis that is optimal for the condition of the patient is performed.

A testing method of the present invention is a method for testing peritoneal function in order to evaluate a condition of a peritoneal dialysis patient, and includes the steps of: repeatedly performing a fluid infusion and a fluid drain of a predetermined amount of peritoneal dialysis fluid in alternation for peritoneal dialysis fluids having different osmotic pressures; analyzing the drain fluid in order to assess an amount of the peritoneal dialysis fluid that is retained within the abdominal cavity of a patient, and a concentration of monitored solutes in the peritoneal dialysis fluid; performing a peritoneal equilibrium test; and performing a blood test in order to assess a change in condition in the blood due to performing the fluid infusion and fluid drain, wherein the step of performing a blood test is executed only once.

BEST MODE FOR CARRYING OUT THE INVENTION

The testing method of the present invention requires a blood test a single time only, allowing the economic and mental burden that the test imposes on patients and the sense of time constraint to be reduced. The method is based on the finding that there is very little change in the blood solute concentration of chronic peritoneal dialysis patients during the 24-hour test period. As a result, a simple testing method that uses test data from a blood sample taken at a representative time during a 24-hour period and that substantially does not affect the precision of analysis by computer simulation was achieved.

In this testing method, it is preferable that the peritoneal equilibrium test is performed last of all the steps, and the blood test is performed immediately before or immediately after the peritoneal equilibrium test, or is performed during the peritoneal equilibrium test. Thus, by taking a single blood sample during testing, preferably when testing has finished, along with a peritoneal equilibrium test, which is a qualitative evaluation method, it is possible to minimize the amount of time spent in the hospital for the purpose of testing.

It is preferable that the monitored solutes for assessing peritoneal function are total protein, albumin, glucose, creatinine, urea, sodium, and chlorine.

It is also preferable that the albumin concentration of the drain fluid is extrapolated based on the total protein concentration of the drain fluid. Thus, the measurement expenses can be kept even lower.

It is preferable that the step of repeating fluid infusion and fluid drain is performed at least three times for each dialysis fluid of respective osmotic pressure. In this case, it is preferable that when the step of repeating fluid infusion and fluid drain is performed a plurality of times using dialysis fluid having the same osmotic pressure, then a dwell time from when the dialysis fluid is infused until when the dialysis fluid is drained is different each time.

With this method, when the change over time in the water removal amount and the change over time in the solute concentration of the drain fluid are expressed as curved lines based on three types of clinical data for different dwell times, it is possible to precisely perform curve fitting for the following reason. That is, this is because in order to perform a high-precision curve fitting it is necessary to predict more precisely the time period during which there is a large change in the curved line, and by setting a large number of test sampling points in the time period where change is largest due to the change over time in the water removal amount, that is, the time period in which the water removal amount is largest, there is better precision of curve fitting. As a result, a peritoneal dialysis simulation, such as one that includes dwell times in which curve fitting is not performed when setting the dose, becomes possible.

Figure 1:
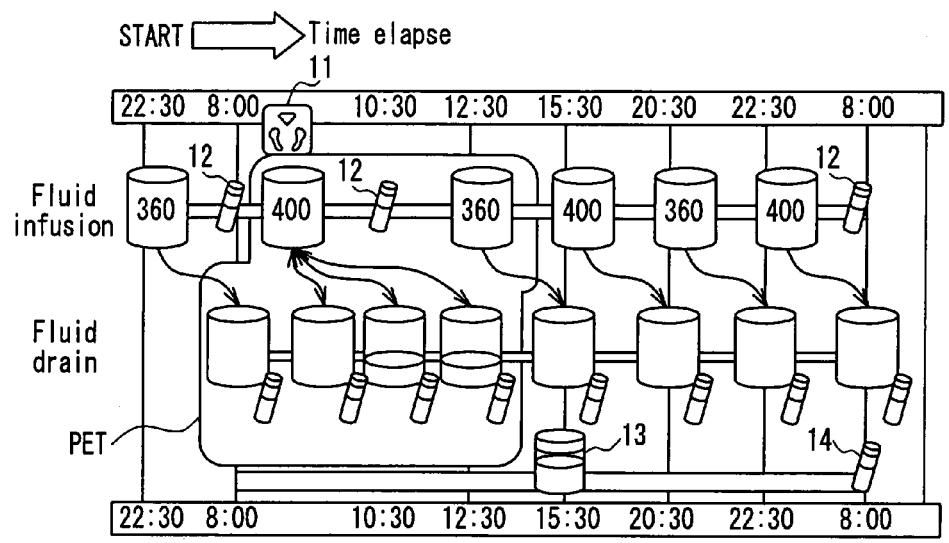
FIG. 1 is a diagram showing the procedure of a conventional example of a method for testing peritoneal function.
Figure 2:
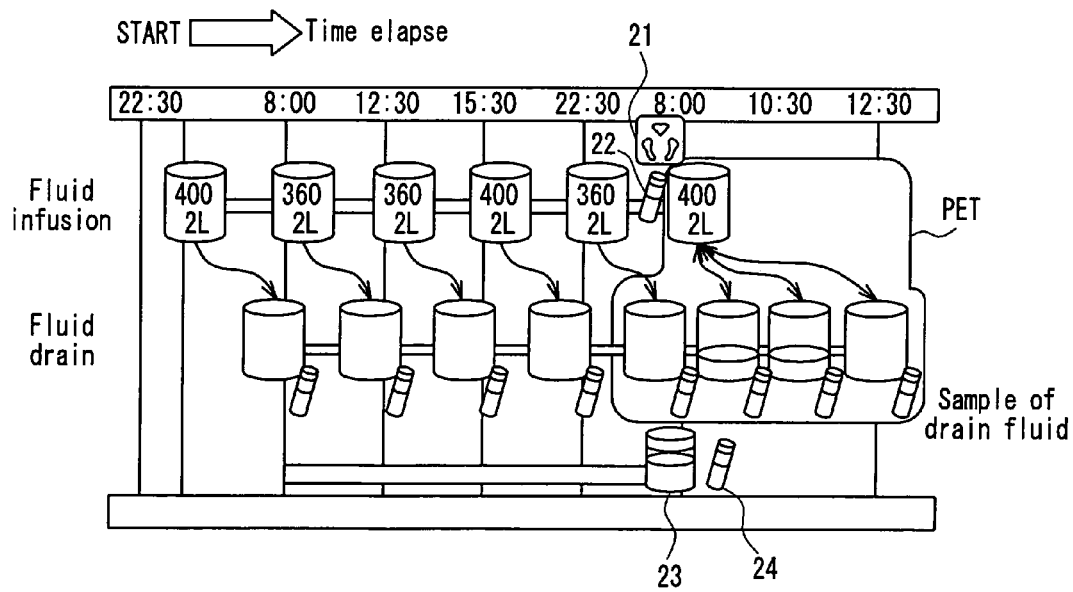
FIG. 2 is a diagram showing the procedure of the method for testing peritoneal function according to an embodiment of the present invention.

Methods for testing peritoneal function according to embodiments of the present invention are described below with reference to the drawings. FIG. 2 shows the procedure of a method for testing peritoneal function according to the present embodiment. FIG. 2, like FIG. 1, shows the timing for "fluid infusion" and "fluid drain" as time elapses. The timing of a body weight measurement 21, a blood draw 22, a urine storage 23, and a urine test 24 are shown in relation to "fluid infusion" and "fluid drain."

Because in the testing method of the present embodiment as well it is necessary to detect the substance balance of monitored solutes (such as urine toxins) and the uptake and drain of water over a 24-hour period, the infusion of dialysis fluid is started from the evening two days prior to the day on which testing ends. However, in the present embodiment, 2L of high osmotic pressure dialysis fluid, that is, the medium osmotic fluid (400), are infused before testing is begun. This is because by infusing a dialysis fluid with high osmotic pressure it is possible to ensure a long dwell time. By contrast, when a low osmotic pressure fluid (360) is infused when testing is started, the dwell time is short, and this requires fluid infusion and fluid drain to be performed during the night and affects the lifestyle of the patient.

The present testing method also differs from the conventional testing method in that the first blood sample is not taken at the point that fluid drain is performed the following morning. Then, infusion of 2L of low osmotic pressure fluid (360) is performed twice, after which 2L of medium osmotic pressure fluid (400) and low osmotic pressure fluid (360) are infused and drained in alternation, and a single blood sample 22 is taken prior to starting the final fluid infusion. Simultaneously, a urine sample is obtained from patients with urine for the urine test 24, and for this reason urine is retained 23. Lastly, a body weight measurement 21 is performed, and then a peritoneal equilibrium test (PET) is performed. In other words, the dialysis fluid that is infused is collected over three collections, and then the entire test is ended.

In this manner, the testing method of the present embodiment is characterized in that the timing and the number of the blood samples taken is different from the conventional method. The reason why this change is possible is explained through the following demonstration experiment.

First, approximately 100 chronic peritoneal dialysis patients were tested using the conventional method for testing peritoneal function shown in FIG. 1, in which blood samples are taken and drained dialysis fluid is stored over a 24-hour period to measure the concentration of monitored solutes in blood and drained fluid during testing. As for the dialysis fluid exchange schedule of the testing, two types of dialysis fluid (low osmotic pressure fluid and medium osmotic pressure fluid) having different osmotic pressures that are adopted based on water removal capability, were each held three times, and each dwell time was different. The reason for doing this is to prevent drops in the precision of analysis by computer simulation and to increase variation in the dosage simulation.

Preferable examples of the monitored solutes that are important for confirming the constancy of chronic peritoneal dialysis patients include total protein, albumin, glucose, creatinine, urea, sodium, and chlorine. The manner in which the concentration of these monitored solutes in the patient's blood changes during the 24-hour testing period was noted.

Figure 3:
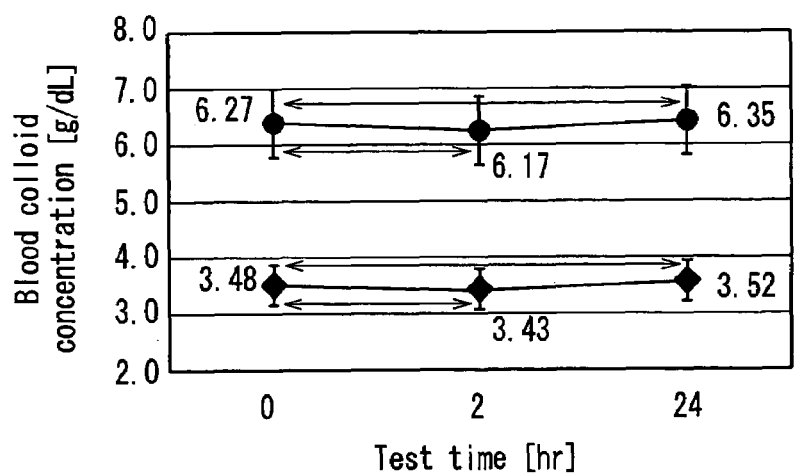
FIG. 3 is a diagram showing the change in blood colloid concentration with respect to test time.

The results of the measurements are shown in FIG. 3, which shows the change over time in the total protein and albumin (colloid) concentration in the blood. In FIG. 3, the solid black circles ● indicate the concentration of total protein in the blood and the solid black diamonds ◆ indicate the concentration of albumin in the blood. It is clear from FIG. 3 that very little change in the total protein concentration and the albumin concentration in the blood was observed over the 24 hour period of the test.

Figure 4:
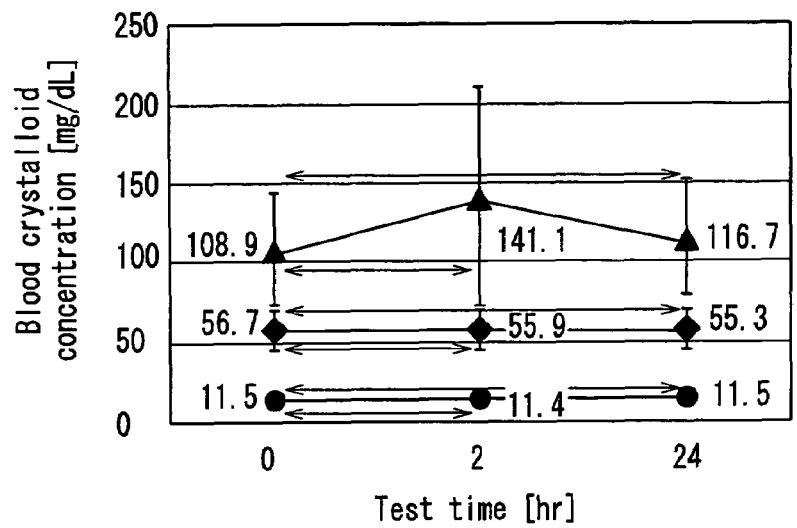
FIG. 4 is a diagram showing the change in blood crystalloid concentration with respect to test time.

FIG. 4 shows the change over test time in the concentration of glucose, creatinine, and urea (crystalloids) in the blood. In FIG. 4, the solid black circles ● indicate the concentration of creatinine in the blood, the solid black diamonds ◆ indicate the concentration of urea in the blood, and the solid black triangles ▲ indicate the concentration of glucose in the blood. As can be understood from FIG. 4, very little change in the creatinine and urea concentration in the blood was observed over the 24-hour period of the test. Also, although the concentration of glucose in the blood rose during testing, hardly any change was observed between that at the start and that at the end of testing.

Figure 5:
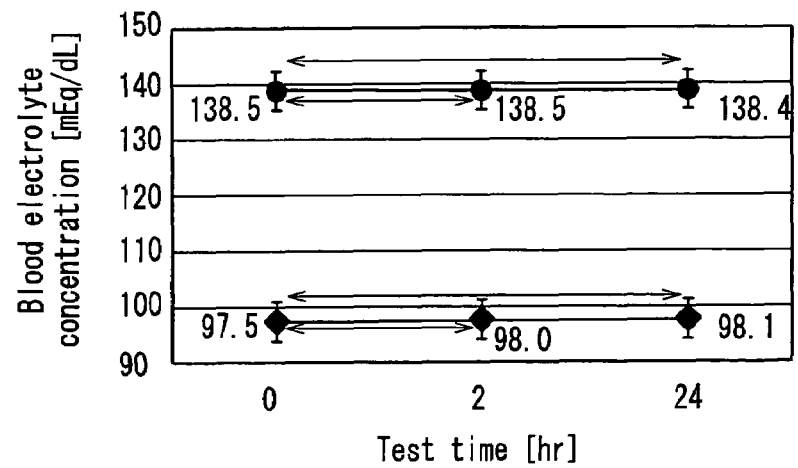
FIG. 5 is a diagram showing the change in blood electrolyte concentration with respect to test time.

FIG. 5 shows the change in blood concentration of sodium and chlorine (electrolytes) during testing. In FIG. 5, the solid black circles ● indicate the concentration of sodium in the blood and the solid black diamonds ◆ indicate the concentration of chlorine in the blood. It is clear from FIG. 5 that very little change in the concentration of sodium and chlorine in the blood was observed over the 24-hour test period.

From the above it is clear that there is very little change in the blood concentration of all of the monitored solutes, these being total protein, albumin, glucose, creatinine, urea, sodium, and chlorine, which are regarded as the monitored solutes that are important for confirming the constancy of chronic peritoneal dialysis patients, between that at the start of testing and that after the 24-hour test period. Consequently, it is conceivable that obtaining a blood and urine sample only once either at the start of testing or after the 24-hour test period would be sufficient.

Here, in consideration of patient convenience, it is necessary to take a blood sample and perform the peritoneal equilibrium test (PET) at a hospital, and ultimately to submit the samples of drained dialysis fluid to the hospital. Taking this into consideration, when a blood sample is taken and the PET test is performed at the start of testing, the patient is required to travel to the hospital twice, and this is not preferable. On the other hand, because the storage of drained dialysis fluid is possible at home, if the patient were to bring drained dialysis fluid samples to the hospital and have blood drawn after testing is finished, it would not be necessary for the patient to be admitted to the hospital. Consequently, as shown in FIG. 2, if the blood and urine samples 22, 24 are obtained and the PET is performed in the hospital when the test sequence has finished, then by the patient coming to the hospital only a single time on the final day, all of the tests can be performed. Thus, the patient is freed from time constraints and the mental and economic burden on the patient can be reduced.

It should be noted that, as shown in FIG. 3, there is an experimentally clear positive correlation between the albumin concentration of the drain fluid and the total protein concentration of the drain fluid. Consequently, the albumin concentration of the drain fluid, which is expensive to measure, can be extrapolated using the total protein concentration of the drained fluid, which is inexpensive to measure. In other words, by measuring only the total protein concentration of the drain fluid and calculating the albumin concentration of the drain fluid without actually measuring it, the test results can be obtained.

Figure 6:
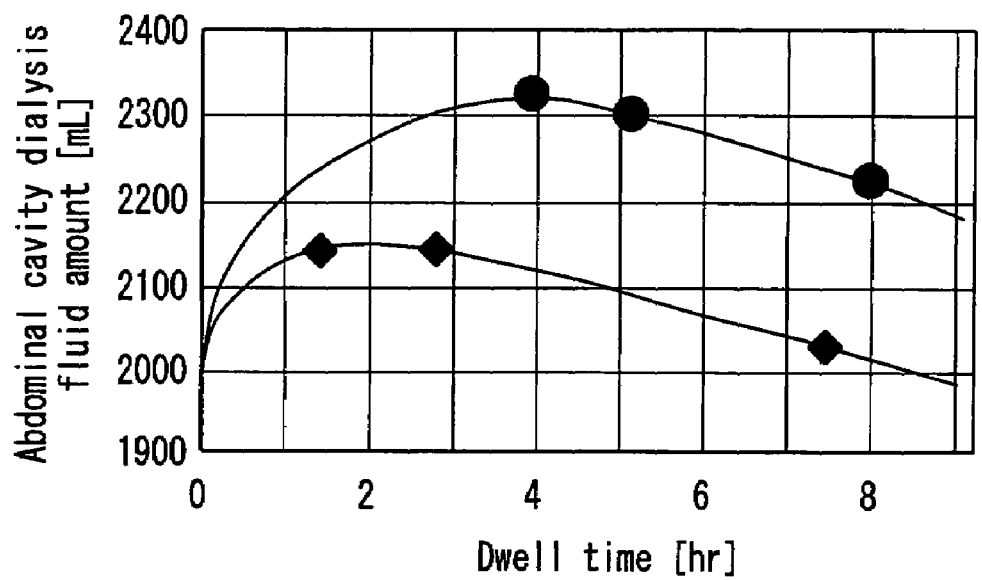
FIG. 6 is a diagram showing the relationship between the amount of dialysis fluid within the abdominal cavity and dwell time.
Figure 7:
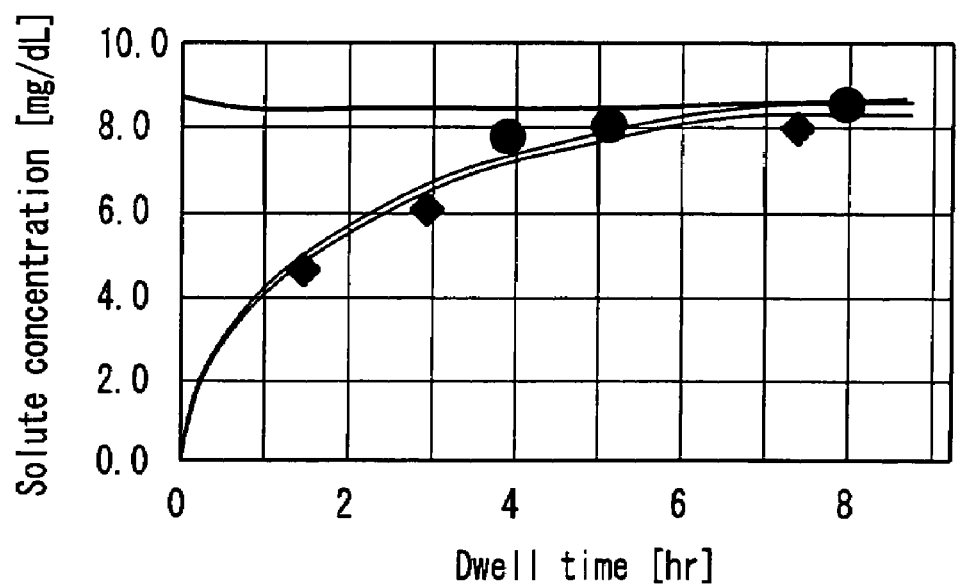
FIG. 7 is a diagram showing the relationship between solute concentration and dwell time.

With the testing method according to this embodiment, it is possible to collect the water removal amount and the solute concentration of the drain fluid as temporally discontinuous clinical data on the low osmotic pressure fluid and the medium osmotic pressure fluid. FIG. 6 and FIG. 7 respectively show an example of the data on the water removal amount (corresponding to amount of abdominal cavity dialysis fluid) and the solute concentration of the drain fluid that are collected using this testing method, plotted against dwell time. In FIG. 6, the solid black circles ● indicate the amount of abdominal cavity dialysis fluid in the case of the dialysis fluid having a high osmotic pressure (medium osmotic pressure fluid) and the solid black diamonds ◆ indicate the amount of abdominal cavity dialysis fluid in the case of the dialysis fluid having a low osmotic pressure (low osmotic pressure fluid). In FIG. 7, the solid black circles ● indicate the solute concentration in the case of the dialysis fluid having a high osmotic pressure (medium osmotic pressure fluid), the solid black diamonds ◆ indicate the solute concentration in the case of the dialysis fluid having a low osmotic pressure (low osmotic pressure fluid), and the thick solid lines each indicate the solute concentration of the blood.

With the testing method of the present embodiment, clinical data are collected for dwell times of three different lengths, and dialysis fluids with different osmotic pressures are infused in alternation. This is to prevent excessive water removal before it occurs by continuously using dialysis fluid having high osmotic pressure. Consequently, in accordance with more specific conditions, the infusion of low osmotic pressure fluid can be partially continuous, but the low osmotic pressure fluid and the medium osmotic pressure fluid are infused in alternation so that the infusion of medium osmotic fluid is not continuous. According to these conditions, in the procedure shown in FIG. 2, it is possible to switch the (12:30) infusion of low osmotic pressure fluid (360) and the (15:30) infusion of medium osmotic pressure fluid (400).

Also, in the present embodiment, at the end of the step of alternately repeating the infusion of dialysis fluids having different osmotic pressures, that is, when the peritoneal equilibrium test is started, the dialysis fluid with the relatively higher osmotic pressure is infused. This is because for the peritoneal equilibrium test it is necessary to infuse the dialysis fluid having the higher osmotic pressure. The reason for this is as follows. In patients with advanced peritoneum permeability, there is little hope that sufficient water removal will occur with the peritoneal dialysis fluid having the lower osmotic pressure. Consequently, with relatively short (for example, four hours) dwell times, the amount of urine toxin that is removed reaches the removal limit, and accurate test values cannot be obtained. On the other hand, with the dialysis fluid having the higher osmotic pressure, the urine toxin removal limit is higher than that of the dialysis fluid having the lower osmotic pressure. For this reason, the removal limit is not reached in a short dwell time, even for patients with advanced peritoneum permeability. Consequently, if the dialysis fluid having the higher osmotic pressure is used, then accurate test values can be obtained regardless of the patient's peritoneum permeability. Thus, it is preferable that the dialysis fluid having the higher osmotic pressure is infused last in the step of alternately repeating fluid infusion and fluid drain.

Also, in this embodiment, the dialysis fluid having the higher osmotic pressure is infused first in the step of alternately repeating the infusion of dialysis fluids having different osmotic pressures. This is because a long dwell time can be secured if the dialysis fluid having the higher osmotic pressure is infused, and this is suited for starting the step of repeated fluid infusion in the evening. By contrast, the dwell time is short when the dialysis fluid having the lower osmotic pressure is infused, and this requires fluid infusion and drain to be carried out at short intervals and affects the lifestyle of the patient. Thus, it is preferable that the dialysis fluid having the higher osmotic pressure is infused first in the step of repeating fluid infusion and fluid drain.

As illustrated above, the present embodiment achieves a simple testing method that uses test data from a single blood sample taken at a representative time during a 24-hour period, without substantially affecting the precision of analysis by computer simulation, based on the finding that there is very little change in the blood solute concentration in chronic peritoneal dialysis patients over a 24-hour test period. As a result, the feeling of time confinement and the economic and mental burden that the test imposes on patients can be reduced.

Also, by taking a blood sample only once during testing, preferably when testing is finished, along with a peritoneal equilibrium test (PET), which is a qualitative evaluation method, it is possible to minimize the amount of time spent in the hospital for the purpose of testing.

INDUSTRIAL APPLICABILITY

The method for testing peritoneal function of the present invention achieves a simple testing method that uses test data from a single blood sample taken at a representative time during a 24-hour period, without substantially affecting the analysis precision of the computer simulation. As a result, it is possible to reduce the feeling of time confinement and the economic and mental burden that the test imposes on patients.

The invention claimed is:

1. A method for testing peritoneal function in order to evaluate the condition of a peritoneal dialysis patient, comprising the steps of:
    alternately and repeatedly infusing and draining with a first peritoneal dialysis fluid having a first osmotic pressure and a second peritoneal dialysis fluid having an osmotic pressure lower than the first osmotic pressure;
    analyzing the drain fluid in order to assess both the amount of the peritoneal dialysis fluid that is retained within the abdominal cavity of a patient, and the concentration of monitored solutes in the peritoneal dialysis fluid for each time of the fluid drain;
    performing a peritoneal equilibrium test, by infusing a dialysis fluid, repeating for predetermined times and at predetermined time intervals draining the dialysis fluid, sampling some of the drained fluid, returning the drained fluid to the patient, and then draining the dialysis fluid; and
    performing a blood test in order to assess concentrations of the monitored solutes; wherein the fluid infusion and the fluid drain is performed at least three times for each of the dialysis fluids of the respective osmotic pressure, a dwell time from when the dialysis fluid is infused until when the dialysis fluid is drained being set to be different each time when using dialysis fluid having the same osmotic pressure,
    the repetition of the fluid infusion and the fluid drain is performed in the order such that the dialysis fluid of the higher osmotic pressure is used for the first and the last times,
    the step of performing the blood test is executed only once; and
    the peritoneal equilibrium test is performed last of all the steps, and the blood test is performed immediately before the peritoneal equilibrium test, or is performed during the peritoneal equilibrium test.

2. The method for testing peritoneal function according to claim 1,
    wherein the monitored solutes for assessing peritoneal function are total protein, albumin, glucose, creatinine, urea, sodium, and chlorine.

3. The method for testing peritoneal function according to claim 2,
    wherein the albumin concentration of the drain fluid is extrapolated based on the total protein concentration of the drain fluid.

* * * * *